(12) United States Patent
Priefer et al.

(10) Patent No.: US 9,921,209 B2
(45) Date of Patent: Mar. 20, 2018

(54) BREATH ACETONE MONITOR AND METHOD OF DETECTING BREATH ACETONE

(71) Applicant: Western New England University, Springfield, MA (US)

(72) Inventors: Ronny Priefer, Wilbraham, MA (US); Michael J. Rust, Springfield, MA (US)

(73) Assignee: WESTERN NEW ENGLAND UNIVERSITY, Springfield, MA (US)

( * ) Notice: Subject to any disclaimer, the term of this patent is extended or adjusted under 35 U.S.C. 154(b) by 0 days.

(21) Appl. No.: 15/411,363

(22) Filed: Jan. 20, 2017

(65) Prior Publication Data

US 2017/0131260 A1   May 11, 2017

Related U.S. Application Data

(62) Division of application No. 14/529,336, filed on Oct. 31, 2014, now Pat. No. 9,581,585.

(60) Provisional application No. 61/904,633, filed on Nov. 15, 2013.

(51) Int. Cl.

| | |
|---|---|
| G01N 33/00 | (2006.01) |
| G01N 33/497 | (2006.01) |
| G01N 21/31 | (2006.01) |
| A61B 5/08 | (2006.01) |
| A61B 5/097 | (2006.01) |
| A61B 5/145 | (2006.01) |
| A61B 5/00 | (2006.01) |
| A61B 10/00 | (2006.01) |

(52) U.S. Cl.
CPC ........... *G01N 33/497* (2013.01); *A61B 5/082* (2013.01); *A61B 5/097* (2013.01); *A61B 5/14532* (2013.01); *A61B 5/7278* (2013.01); *G01N 21/31* (2013.01); *A61B 2010/0087* (2013.01)

(58) Field of Classification Search
None
See application file for complete search history.

(56) References Cited

U.S. PATENT DOCUMENTS

| | | |
|---|---|---|
| 2012/0136268 A1 | 5/2012 | Li et al. |
| 2015/0177224 A1 | 6/2015 | Priefer et al. |

FOREIGN PATENT DOCUMENTS

| | | |
|---|---|---|
| WO | 2014076493 A1 | 5/2014 |

OTHER PUBLICATIONS

Banach, N.M., et al.; A Portable Spectrophotometer-Based Breathalyzer for Point-of-Care Testing of Diabetic Patients; 39th Annual Northeast Bioengineering Conference; 2013; pp. 245-246.
(Continued)

*Primary Examiner* — Xiaoyun R Xu
(74) *Attorney, Agent, or Firm* — Cantor Colburn LLP

(57) ABSTRACT

A breath acetone meter is provided. The blood glucose meter includes a receiver comprising a first polymer and a second plurality of layers arranged in an alternating arrangement. The receiver is configured to receive a breath sample from a user. The first plurality of layers and second plurality of layers being configured to interact in response to the level of acetone in the breath sample. The breath acetone meter further including a light source arranged to emit a light onto the receiver. A sensor is arranged to receive the light and output a voltage in response to receiving the light, wherein the voltage is proportional to an amount of acetone in the breath sample.

6 Claims, 5 Drawing Sheets

(56) References Cited

OTHER PUBLICATIONS

International Search Report and the Written Opinion of the International application No. PCT/US2014/064029; dated Jan. 14, 2015; dated Feb. 5, 2015; pp. 1-7.
Priefer, Ronny, et al.; Multilayer Film Preparation of Poly(4-vinylphenol) From Aqueous Media; Surface and Coatings Technology; 2008; vol. 202; pp. 6109-6112.
Extended European Search Report for Application No. 14861508.1 dated May 8, 2017; 9 pgs.
Ruan, H., et al: "Nanostructured Fiber Optic Sensors for Detection of Volatile Organic Compounds in Breath", SPIE, PO Box 10 Bellingham WA 98227-0010 USA, Dec. 31, 2006 (Dec. 31, 2006), XP040218423.
Worrall, Adam D., et al.: "Portable method of measuring gaseous acetone concentrations", Talanta Elsevier, Amsterdam, NL, vol. 112, Mar. 31, 2013 (Mar. 31, 2013), pp. 26-30, XP028550070.

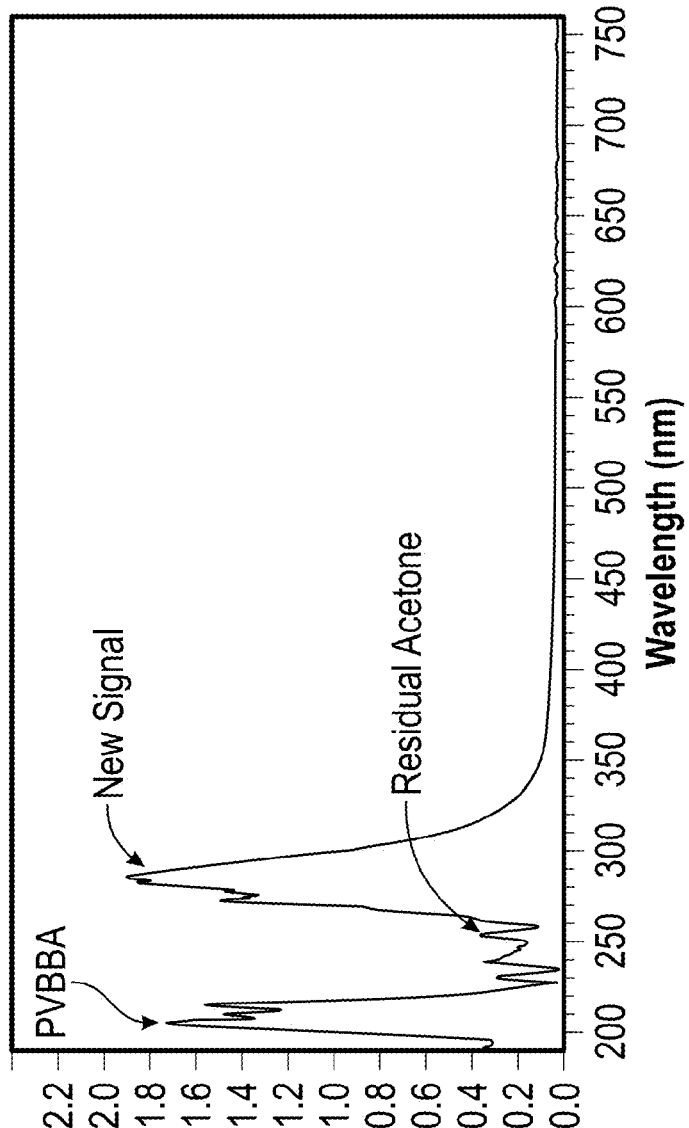
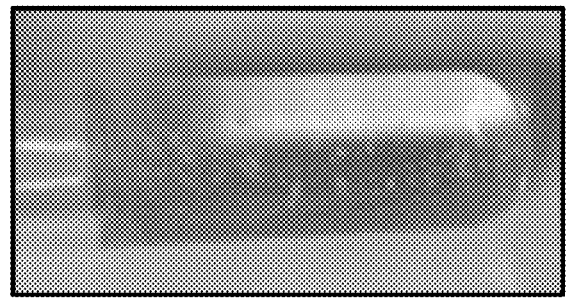
FIG. 4B
FIG. 4A

BREATH ACETONE MONITOR AND METHOD OF DETECTING BREATH ACETONE

CROSS REFERENCE TO RELATED APPLICATIONS

The present application is a divisional application of U.S. application Ser. No. 14/529,336 filed on Oct. 31, 2014, which is a non-provisional application of U.S. Provisional Application No. 61/904,633 filed on Nov. 15, 2013, the contents of both of which are incorporated herein in their entirety.

BACKGROUND

The subject matter disclosed herein relates to a breath acetone monitor and, more particularly, to a breath acetone monitor that relates a user's blood sugar levels based on an acetone level in their breath.

Diabetes can be a life-long disease which requires continuous blood-glucose monitoring. Currently technology involves sticking the patient's finger with a sharp implement to obtain a sample of blood. The blood sugar level may then be directly measured from the sample. These techniques, albeit good, do have draw-backs, in particular that it is an invasive technique which causes discomfort to the individual. Therefore, low compliance can ultimately lead to other health issues. Approaches have been proposed to develop a portable, hand-held, noninvasive monitoring device to detect the biomarker, such as acetone (which has been shown to correlate with blood-glucose levels), found in the breath of diabetics.

Accordingly, while existing blood sugar level techniques are suitable for their intended purposes the need for improvement remains, particularly in providing a noninvasive blood glucose monitor.

BRIEF DESCRIPTION

According to one aspect of the invention, an acetone monitor has been provided that detects acetone using a multilayer thin film approach. By creating films of poly(4-vinylbenzeneboronic acid) and poly(allylamine hydrochloride), breath acetone reacts with these two polyelectrolytes via a Petasis reaction, or derivatives thereof. This causes the polymers to interact, altering the physicochemical nature of the film, which provides a quantification of the acetone, and thus a correlated physiologic parameter, such as the blood-glucose levels for example, may be determined in a non-invasive manner.

According to another aspect of the invention, a breath acetone meter is provided. The meter comprising: a receiver comprising a first polymer and a second polymer, the receiver being configured to receive a breath sample from a patient, the first polymer and second polymer being configured to interact in response to the level of acetone in the breath sample; a light source arranged to emit a light onto the receiver; and a sensor arranged to receive the light and output a voltage in response to receiving the light, wherein the voltage is correlated to an amount of acetone in the breath sample.

According to yet another aspect of the invention, a method of measuring breath acetone is provided. The method comprising: receiving a patient's breath with a meter device, the meter device having a receiver comprising a first polymer and a second polymer, the meter device further having a light source and a sensor; interacting the first polymer with the second polymer in response to receiving the patient's breath; emitting a light from the light source onto the receiver; receiving the light on the sensor; generating a voltage with the sensor; and determining an amount of acetone based at least in part on the voltage.

According to yet another aspect of the invention, another breath acetone meter is provided. The meter comprising: a receiver having a first plurality of polymer layers and a second plurality of polymer layers, the receiver being arranged to receive a breath sample from a patient, the first plurality of layers and second plurality of layers being formed from a polymer material that is configured to interact in response to the level of acetone in the breath sample; a light source arranged on one side of the receiver; a second arranged on side of the receiver opposite the light source, the sensor configured to receive light from the light source and output a voltage signal in response; and a controller coupled to receive the voltage signal, the controller including a processor that is responsive to executable computer instructions when executed on the processor for determining a physiological parameter level in response to receiving the voltage signal.

These and other advantages and features will become more apparent from the following description taken in conjunction with the drawings.

BRIEF DESCRIPTION OF THE DRAWING

The subject matter, which is regarded as the invention, is particularly pointed out and distinctly claimed in the claims at the conclusion of the specification. The foregoing and other features, and advantages of the invention are apparent from the following detailed description taken in conjunction with the accompanying drawings in which:

FIG. 4A is an illustration of the interaction of the reaction of PVBBA with poly(allylamine hydrochloride) (PAH) after being exposed to acetone in water;

FIG. 4B is an illustration of an absorption profile measured for the sample of FIG. 4A;

The detailed description explains embodiments of the invention, together with advantages and features, by way of example with reference to the drawings.

DETAILED DESCRIPTION

Embodiments of the subject invention include a breath acetone monitoring technology that detects acetone using a multilayer thin film approach. By creating films of poly(4-vinylbenzeneboronic acid) (PVBBA) and poly(allylamine hydrochloride) (PAH), breath acetone reacts with these two polyelectrolytes via a Petasis reaction (FIG. 4). This causes polymers to interact together, altering the physicochemical nature of the film, which provides a quantification of the acetone, and thus the level of a correlated physic logical parameter, such as blood-glucose levels for example, in a non-invasive manner. In one embodiment, the interaction of the polymers is a cross-linking of poly(4-vinylbenzeneboronic acid) and poly(allylamine hydrochloride) layers.

Figure 1:
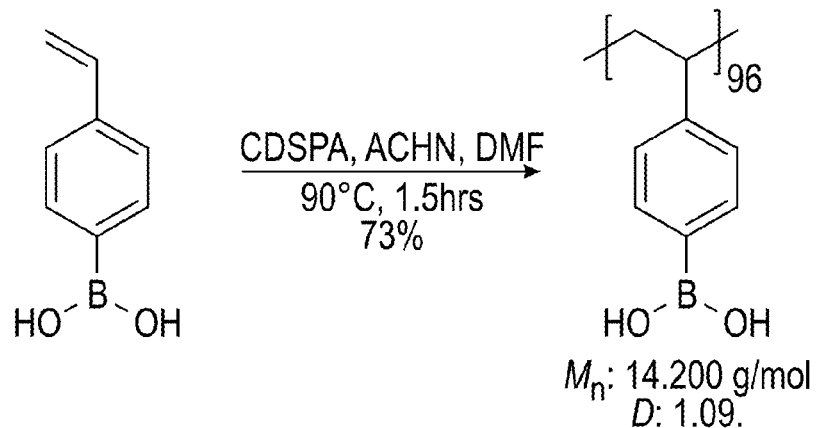
FIG. 1 is an illustration of a mixture used for synthesis poly(4-vinylbenzeneboronic acid (PVBBA)
Figure 2:
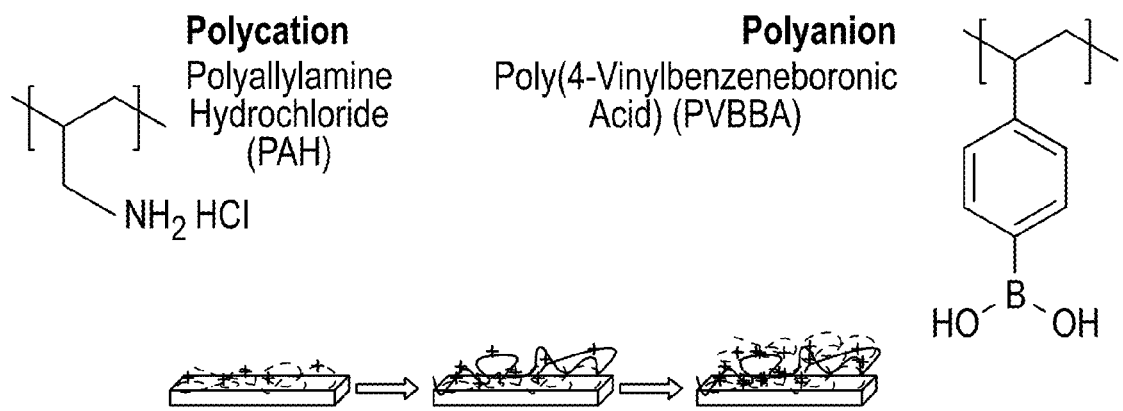
FIG. 2 is another illustration of the film buildup of PVBBA with PAH.
Figure 3:
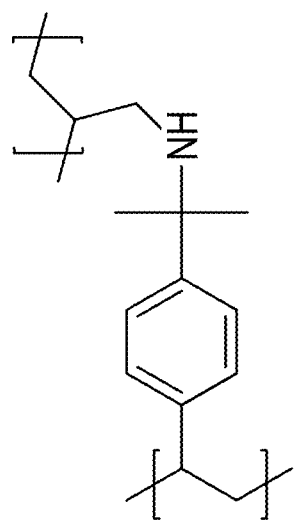
FIG. 3 is an illustration of one embodiment of a Petasis reaction to allow for the interaction of PVBBA with PAH.
Figure 3:
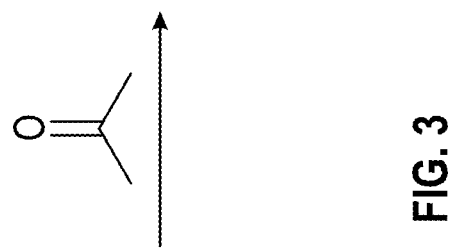
Figure 3:
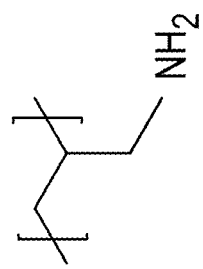
Figure 3:
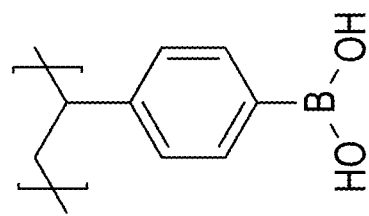

In one embodiment, to synthesis poly(4-vinylbenzeneboronic acid) 4-vinylbenzeneboronic acid, 4-cyano-4-[(dodecylsulfanylthio-carbonyl)sulfanyl] pentanoic acid, and 1,1'-azobis(cyclohexane-carbonitrile), were mixed in a 1.0: 0.045:0.0016 ratio in DMF, and subjected the mixture to three freeze-thaw cycles, sealed under vacuum and heated to 90° C. for 1.5 hrs (FIG. 1). The mixture was precipitated twice with ether, and vacuum dried at overnight, to afford the polymer with a $M_n$ of 14,200 g/mol and a polydispersity of 1.09. A 0.002 M solution of this polymer and poly(allylamine hydrochloride) with a salt concentration of 0.1 M were formulated, and using layer-by-layer assembly, films of up to 50 layers were produced. It should be appreciated that these layers may also be formed using other techniques, such as spraying, layer-by-layer dipping, spin casting, and impinging jets for example. These surfaces were subjected to acetone vapor and the spectroscopic differences in these films were analyzed (FIG. 4B). It is contemplated that the number of layers may range from 10-50 layers.

When a small amount of acetone was added to a 1:1 ratio of these two poly-electrolytes, a slight coloring of the solution and a precipate was observed (FIG. 4A). The UV-Vis profiles of the individual polyelectrolyte systems and that of the mixed system, are different. The PAH, PVBBA mixed system with acetone has a new signal at a wavelength of approximately 295 nm (FIG. 4B). Therefore, it is possible to spectroscopically observe the amount of change in the multilayered system, and thus if calibrated, the actual amount of acetone.

With the wavelength for analysis in hand we next evaluated the ability to cross-link PAH and PVBBA on coated slides. UV-transmitting poly(methyl methacrylate) (UVT-PMMA) slides were coated with a 10-layer system of PAH/PVBBA at pH 11.5 and was then exposed to acetone/water vapor for 5 minutes. The slide was next subjected to the light emitted by a diode (LED300W, Thorlabs) with a peak wavelength of 300±5 nm. The transmitted light was detected by a UV-photosensor (model GUVA-T11 manufactured by Genicom Co. Ltd) with an integrated transimpedance amplifier that produced a voltage output as a function of absorption (FIG. 5). Upon exposure of the 10-layered PAH/PVBBA coated UVT-PMMA slide to acetone vapor, crosslinking of the PAH/PVBBA film occurred. Data from preliminary testing with the first generation prototype are displayed in FIG. 6. The results demonstrate the expected decreased output voltage for the acetone exposed PAH/PVBBA cross-linked UVT-PMMA slide versus the unexposed PAH/PVBBA slide (FIG. 6). This indicates that the exposed slide has increased absorption at 300 nm. To ensure that what was being observed is an irreversible process, the slide was rerun 24 hrs later and obtained the identical output. These qualitative results suggest that it will be possible to quantify the Petasis reaction with this technology and therefore obtain accurate acetone concentrations.

Figure 5A:
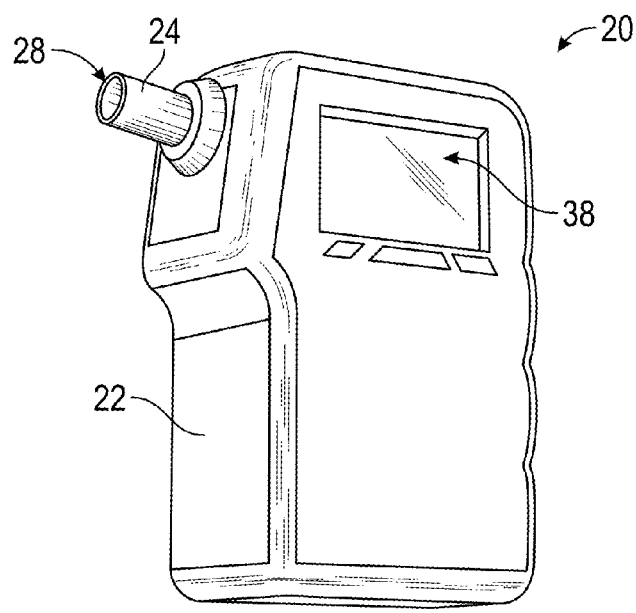
FIGS. 5A and 5B are illustrations of a spectrophotometer based breath acetone meter.
Figure 5B:
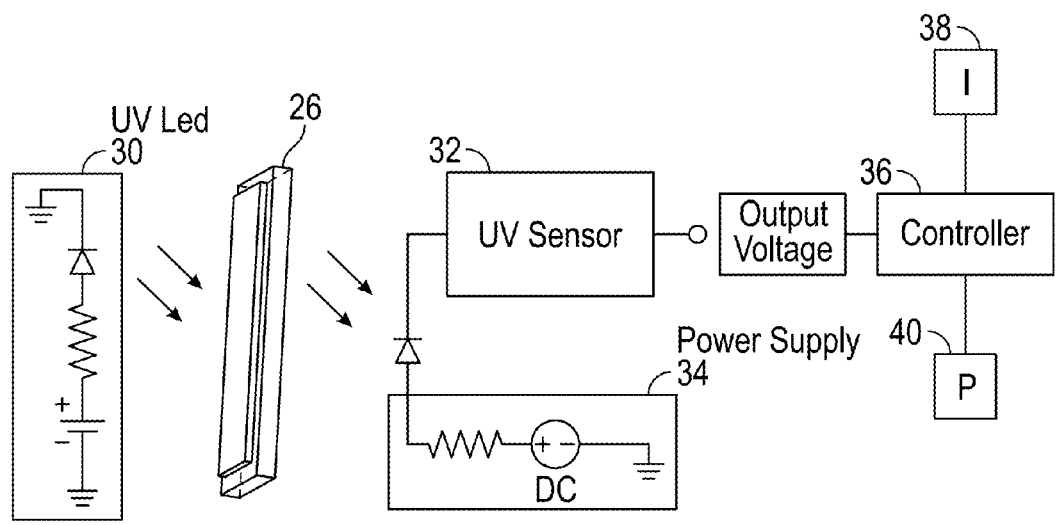
Figure 6:
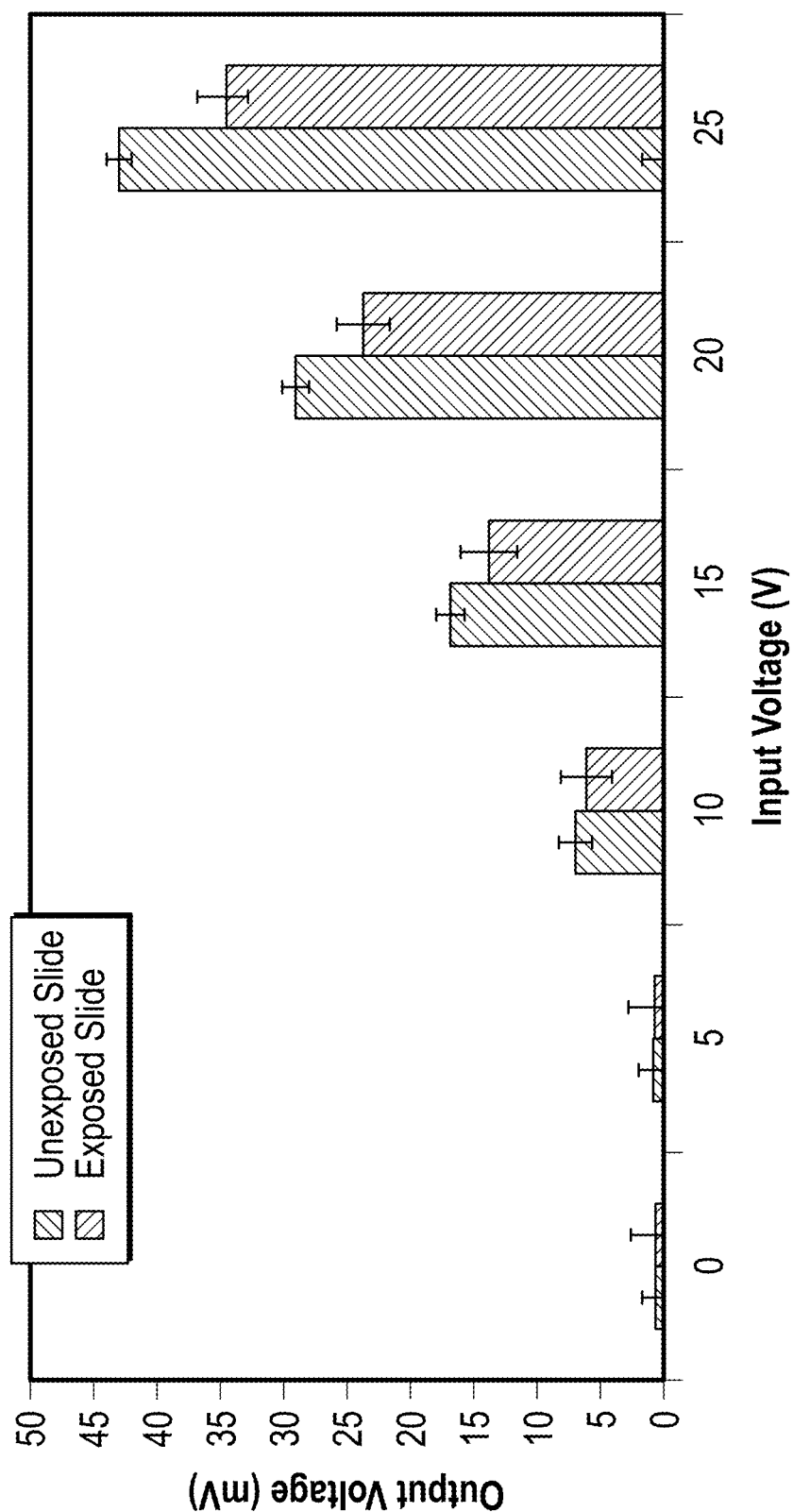
FIG. 6 illustrates a graphical plot of the output voltage as a function of input voltage from the results of testing the breath acetone meter of FIGS. 5A and 5B.

In one embodiment, shown in FIG. 5A, a breath acetone measurement device 20 is provided that is sized and shaped to be held by a user to detect acetone levels in their breath. The device 20 may include a housing 22 with an inlet or mouth piece 24 at one end. The mouth piece 24 is in fluid communication with a receiver 26 (FIG. 5B). The mouth piece 24 may include a removable sheath (not shown) that may be disposed of after each use to allow multiple persons to use the same device 20, or to allow use in a medical environment (e.g. a hospital, doctors office or ambulance for example). The mouth piece 24 may including an opening 28 that defines a conduit that allows the users breathe sample to be directed onto the receiver 26. As discussed herein, the receiver may be formed from a first plurality of polymer layers and a second plurality of polymer layers that interact with each other presence of acetone in the user's breath sample. The polymer layers may be made from a polymer such as PVBBA family of polymers and PAH family of polymers or derivatives thereof. In one embodiment, the receiver 26 is removably coupled to the device 20 and may be replaced after each measurement operation.

A light source 30 is arranged on one side of the sensor 26 to direct light onto the receiver 26. In the exemplary embodiment, the light source 30 is a UV-Vis light source that emits a light having a peak wavelength of 300 nanometers. A sensor 32 is arranged on a side of the receiver 26 opposite the light source 30. The sensor 32 is arranged to receive light from the light source. The sensor 32 is coupled to a power supply 34 that provides an input voltage to the sensor 32. The sensor 32 is configured to provide an output voltage in response to receiving light from the light source 30 that has passed through the receiver 26. It should be appreciated that the amount of acetone in the breath sample will change the amount of interaction between the first plurality of layers and the second plurality of layers and thus change the amount of light from the light source 30 that is received by the sensor 32.

In one embodiment, the output voltage signal is transmitted to a controller 36. Controller 36 is a suitable electronic device capable of accepting data and instructions, executing the instructions to process the data, and presenting the results. Controller 36 may accept instructions through user interface 38, or through other means such as but not limited to electronic data card, voice activation means, manually-operable selection and control means, radiated wavelength and electronic or electrical transfer. Therefore, controller 36 can be a microprocessor, microcomputer, a minicomputer, an optical computer, a board computer, a complex instruction set computer, an ASIC (application specific integrated circuit), a reduced instruction set computer, an analog computer, a digital computer, a molecular computer, a quantum computer, a cellular computer, a superconducting computer, a supercomputer, a solid-state computer, a single-board computer, a buffered computer, a computer network, a desktop computer, a laptop computer, a scientific computer, a scientific calculator, a cellular phone or a hybrid of any of the foregoing.

Controller 36 is capable of converting the analog voltage level provided by sensor 32 into a digital signal indicative of the amount of acetone in the breath sample received via the mouth piece 24. In one embodiment, sensor 32 may be configured to provide a digital signal to controller 36, or an analog-to-digital (A/D) converter (not shown) maybe coupled between sensor 32 and controller 36 to convert the analog signal provided by sensor 32 into a digital signal for processing by controller 36. Controller 36 uses the digital signals act as input to various processes for controlling the device 20 or displaying results to the user. The digital signals represent one or more device 20 data including but not limited to the blood sugar level of the user for example.

In general, controller 36 accepts data from sensor 32 and is given certain instructions for the purpose of comparing the data from sensor 32 to predetermined parameters to correlate the data with a physiological parameter level, such as blood sugar level for example. Controller 36 may display results of the physiological parameter level on the user interface 38. The controller 36 compares the physiological parameter level to predetermined variances (e.g. low sugar level or high sugar level for the user) and if the predetermined variance is exceeded may generate a signal that may be used to indicate an alarm to the user. In one embodiment, the controller 36 may be configured to transmit an alert signal to a remote computer or to transmit a signal via another communications medium, such as a cellular SMS (text message) signal to a predetermined third party for example.

The data received from sensor 32 may be displayed on a user interface 38 coupled to controller 36. The user interface may be an LED (light-emitting diode) display, an LCD (liquid-crystal diode) display, a CRT (cathode ray tube) display, or the like. A keypad may also be coupled to the user interface for providing data input to controller 36.

The controller 38 may include a processing circuit 40. The processing circuit 40 may include a processor coupled to one or more memory devices. The memory devices may include random access memory (RAM) device, a non-volatile memory (NVM) device or a read-only memory (ROM) device. The processor may also be coupled to one or more input/output (I/O) controllers and a LAN interface device via a data communications bus.

The memory devices store an application code, e.g., main functionality firmware, including initializing parameters, and boot code, for the processor. Application code also includes program instructions for causing processor to execute any operation control methods, including starting and stopping operation, determining the level of the physiologic parameter based on the output voltage signal, and generation of alarms. The application code may create an onboard telemetry system may be used to transmit operating information between the device 20 and a remote terminal location and or/receiving location (e.g. a doctor's office, a hospital, a medical monitoring center, or a family member). The information to be exchanged remote computers and the controller 36 may include but is not limited to the output voltage level and the physiological parameter level.

It should be appreciated that the controller 36 may be remotely located from the housing 22. In this embodiment, the device 20 may include a communications circuit (e.g. WiFi, Bluetooth, cellular, Ethernet) that transmits the output voltage signal to the remotely located controller 36. In one embodiment, the controller 36 may be a cellular phone that connects to the device 20 via a wired or wireless communications medium.

In operation, the user puts their mouth on the mouth piece 24 and blows a small amount of their breath into the opening 28. Their breath sample travels onto the housing 22 and onto the receiver 26. The acetone in the breath sample causes the first plurality of layers and second plurality of layers in the receiver 26 to interact, such as by cross-linking for example. This interaction changes the transmittance of light through the receiver 26. Once the breath sample is received on the receiver 26, the light source 30 is activated to emit and direct light onto the receiver 26. A portion of the emitted light is received on the sensor 32 and an output voltage signal is transmitted to the controller 36. The controller 36 then determines, such as with the processing circuit 40 for example, a level of the user's physiological parameter. In one embodiment, the processing circuit 40 may determine the level of the physiological parameter from a look-up table stored in memory, where the look-up table includes data that correlates the output voltage level to a physiological parameter level. In one embodiment, the determination of the physiological parameter level may also be based on the user's characteristics, such as weight, age or physical condition for example. Once the level of the physiological parameter is determined, it may be displayed to the user via the user interface 38.

It should be appreciated that the subject invention provides advantages in allowing the determination of blood glucose levels in a patient's blood from the output voltage of the sensor. Embodiments of the subject invention provide further advantages in allowing the determination of blood glucose levels in a non-invasive manner. Further, while embodiments herein describe the use of acetone levels in a user's breath with blood glucose levels, this is for exemplary purposes and the claimed invention should not be so limited. In other embodiments, acetone levels may be correlated with levels of other physiological parameters conditions.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

The invention claimed is:

1. A method of measuring breath acetone, the method comprising:
   receiving a sample of a user's breath with a meter device, the meter device having a receiver comprising a first polymer layer and a second polymer layer, the meter device further having a light source and a sensor, wherein the first polymer layer and the second polymer layer are each formed from a plurality of layers;
   interacting the first polymer layer with the second polymer layer to change a light absorption level of the receiver in response to receiving the patient's breath, wherein the interacting includes cross-linking the first polymer layer and the second polymer layer;
   emitting a light from the light source onto the receiver;
   receiving the light on the sensor;
   generating a voltage with the sensor; and
   determining an amount of acetone based at least in part on the voltage.

2. The method of claim 1 further comprising determining a physiological parameter based at least in part on the determined amount of acetone.

3. The method of claim 2 wherein the determined physiological parameter is a blood sugar level.

4. The method of claim 1 further comprising disposing the first plurality of layers and the second plurality of layers in an alternating arrangement.

5. The method of claim 4 wherein each of the first plurality of layers and the second plurality of layers includes between 10-50 layers.

6. The method of claim 2 further comprising:
   forming the first plurality of layers from poly(4-vinylbenzeneboronic acid) family of polymers; and
   forming the second plurality of layers from poly(allylamine hydrochloride) family of polymers.

\* \* \* \* \*